United States Patent
Wang (10) Patent No.: US 9,393,003 B2
(45) Date of Patent: Jul. 19, 2016

(54) DEVICE FOR SEALING SINGLE INCISION FROM LAPAROSCOPIC SURGERY

(76) Inventor: Xiaojun Wang, Ningbo (CN)

( * ) Notice: Subject to any disclaimer, the term of this patent is extended or adjusted under 35 U.S.C. 154(b) by 180 days.

(21) Appl. No.: 14/370,363

(22) PCT Filed: Jul. 9, 2012

(86) PCT No.: PCT/CN2012/078338
§ 371 (c)(1),
(2), (4) Date: Jul. 2, 2014

(87) PCT Pub. No.: WO2013/104179
PCT Pub. Date: Jul. 18, 2013

(65) Prior Publication Data
US 2014/0371788 A1    Dec. 18, 2014

(30) Foreign Application Priority Data

Jan. 12, 2012 (CN) .................. 2012 2 0012211 U
May 23, 2012 (CN) .................. 2012 1 0163089

(51) Int. Cl.
*A61B 1/00* (2006.01)
*A61B 17/00* (2006.01)
*A61B 17/34* (2006.01)

(52) U.S. Cl.
CPC ......... *A61B 17/0057* (2013.01); *A61B 17/3423* (2013.01); *A61B 2017/00592* (2013.01); *A61B 2017/00606* (2013.01); *A61B 2017/00632* (2013.01); *A61B 2017/3466* (2013.01)

(58) Field of Classification Search
CPC ........... A61B 17/0057; A61B 17/3423; A61B 17/0293; A61B 17/3462; A61B 2017/00637; A61B 2017/3425; A61B 2017/3466; A61B 2017/3447; A61B 2017/3449; A61B 2017/00632; A61B 2017/00592; A61B 2017/00606

USPC .......................... 600/204, 205, 206, 208, 201
See application file for complete search history.

(56) References Cited

U.S. PATENT DOCUMENTS

| | | | |
|---|---|---|---|
| 6,551,270 B1 * | 4/2003 | Bimbo | A61B 17/3421 604/167.03 |
| 2010/0081880 A1 * | 4/2010 | Widenhouse | A61B 17/3462 600/201 |
| 2010/0228090 A1 * | 9/2010 | Weisenburgh, II | A61B 17/3423 600/201 |
| 2010/0228198 A1 * | 9/2010 | Widenhouse | A61B 17/3423 604/167.01 |
| 2010/0249526 A1 * | 9/2010 | Shelton, IV | A61B 17/0293 600/208 |

* cited by examiner

*Primary Examiner* — Melanie Tyson
*Assistant Examiner* — Majid Jamialahmadi
(74) *Attorney, Agent, or Firm* — Wang Law Firm, Inc.

(57) ABSTRACT

A device for sealing a single incision in a laparoscopic surgery, includes: an operating panel located on the top portion of the device, a sleeve located on the bottom portion of the device, a soft connecting portion; two symmetrical handles attached to the external surface of the sleeve; a blocking flange attached to the bottom end of the sleeve; and two clamping portions disposed on the blocking flange. The sleeve is inserted into the wound of the abdominal wall, the blocking flange is positioned inside the abdominal cavity and the soft connecting portion is positioned outside the abdominal cavity. The operating panel rotates around the axis of the soft connecting portion, and the operating holes with seals may avoid air leakage of the abdominal cavity. The device solves the defect that the use of a tubular anastomat in a laparoscopic surgery easily leads to air leakage and inconvenient operation.

7 Claims, 9 Drawing Sheets

DEVICE FOR SEALING SINGLE INCISION FROM LAPAROSCOPIC SURGERY

RELATE APPLICATIONS

This application is a national phase entrance of and claims benefit to PCT Application for Device for Sealing a Single Incision in a Laparoscopic Surgery thereof, PCT/CN2012/078338, filed on Jul. 9, 2012, which claims benefit to Chinese Patent Application 201220012211.3, filed on Jan. 12, 2012 and Chinese Patent Application 201210163089.4, filed on May 23, 2012. The specifications of both applications are incorporated herein by this reference.

FIELD OF THE INVENTION

The present invention relates to a sealing device in laparoscopic surgery, in particular to a device for sealing a single incision in laparoscopic surgery.

DESCRIPTION OF THE PRIOR ART

Minimally invasive surgery, represented by laparoscopic surgery, has developed in three stages in China: resection and functional repair of benign lesion viscera primarily by laparoscopic cholecystectomy in the early 1990s, resection of gastrointestinal malignant tumors from the late 1990s, and rapid development and widespread of the minimally invasive surgery of gastrointestinal tumors from the beginning of the 21st century. Surgery experienced a transition from the conventional laparotomy surgery to the laparoscopic surgery regarded as "The Second Revolution", and is undergoing an evolution from multi-incision laparoscopic surgery to single-incision laparoscopic surgery or even natural orifice transluminal endoscopic surgery without scars left on the body surface in recent years. The transumbilical surgery may generally produce incisions above or below the umbilicus or even longitudinal incisions of the umbilical ring. At present, there are three common approaches for establishing a channel. (1) An integrated Port, accompanied with several fixed or unfixed trocars, may be used, from which instruments may be inserted to be operated. There have been related finished products at abroad, such as Uni-X, R-port, Gelport, etc. This approach has disadvantages that the incisions are large, interference exists between surgical instruments, and it is inconvenient to operate. (2) trocars of different sizes are connected to each other, or simply, trocars are separately inserted from a same incision. This approach has the disadvantages of high probability of air leakage and large interference. Although the approach can use conventional laparoscopic instruments and can be carried out clinically, it is inconvenient to operate. (3) A single trocar having a diameter of 10 mm is inserted into the laparoscope and then fed with air for maintaining the pneumoperitoneum pressure, and the rest laparoscopic instruments are inserted by sharp puncturing. Alternatively, detachable trocars (Patent No. ZL200920078343.4) may be used, and the trocars are withdrawn after assisting in inserting the laparoscopic instruments into the abdominal cavity. Only 10 mm of trocars is reserved during the surgical operation.

A Chinese Patent (Publication No.: CN101129273A published on Feb. 27, 2008), titled Sealer for Abdominal Incision in laparoscopic surgery, disclosed a sealer for sealing incision in a laparoscopic surgery. Such a sealer comprises an elastic liner ring and a soft sleeve. One end of the soft sleeve is connected to the elastic liner ring, while the other end thereof is an opening. The sealer of such a configuration is extruded to the periphery of the incision by the inflation of the soft sleeve to form a seal configuration with the liner ring. However, the sealing of the soft sleeve by bulging is not so reliable; furthermore, as the other end of the soft sleeve is poor in sealing performance, it is likely to have air leakage. As a result, the soft sleeve cannot bulge due to the reduction of pressure therein. Consequently, the extrusion force between the soft sleeve and the periphery of the incision decreases, causing air leakage on the periphery of the incision and influencing the continuation of the operation.

SUMMARY OF THE INVENTION

It is a first object of the present invention to provide a device for sealing a single incision in a laparoscopic surgery, which is convenient to operate and is able to effectively seal and prevent the abdominal cavity from air leakage, thus to solve the defect in the prior art that the use of a tubular anastomat in a laparoscopic surgery easily leads to air leakage and inconvenient operation.

It is a second object of the present invention to provide a device for sealing a single incision in a laparoscopic surgery, which integrates all holes required by multiple surgical tools onto one plate and reduces cuts, thus to solve the deficiency in the prior art that the laparoscopic surgery results in many large incisions and large traumas to patients.

It is a third object of the present invention to provide a device for sealing a single incision in a laparoscopic surgery, which has multiple passages from a single hole and may be widely applied in single-incision laparoscopic surgery, thus to solve the deficiency in the prior art that inserting multiple instruments of the laparoscope into the abdominal cavity from multiple operating holes causes larger trauma.

For achieving the objects, a device for sealing a single incision in a laparoscopic surgery, comprises: a top portion; a bottom portion; an operating panel located on the top portion of the device and with a plurality of sealed operating holes, a sleeve with suitable elasticity located on the bottom portion of the device, having an external surface and a top end and a bottom end, for fitting into the single incision, a soft connecting portion for connecting the operating panel to the sleeve; two symmetrical handles attached to the external surface of the sleeve where the sleeve connects to the soft connecting portion, each handle having a hole; a blocking flange attached to the bottom end of the sleeve; and two clamping portions disposed on the blocking flange under the two handles. As the sleeve has a suitable elasticity, the sleeve deforms and shrinks at first before inserted into the incision, and squeezes the periphery of the incision for sealing under the restoring force after inserted into the incision. The sleeve can deform due to its elasticity. The medical sleeve is generally made of medical polyurethane (or medical silica gel). When inserted, the sleeve and the blocking flange squeeze to generate deformation to be inserted from the incision. When the blocking flange enters the abdominal cavity, the sleeve and the blocking circle restore to their original shape, and the blocking flange adheres to the inner skin wall of the abdominal cavity to form a stopping configuration for preventing the sleeve from coming out. The fitting of each handle and the corresponding clamping portion is convenient for a pair of forceps to clamp the sleeve to make the sleeve deform. The protruded clamping portion is convenient for the ends of the pair of forceps to clamp the sleeve. The hole on each handle is mainly for purpose of positioning a pair of forceps and also allowing the all extrusion force generated by the pair of forceps to act on the sleeve, so that the sleeve is fully squeezed and deformed. There are multiple operating holes on the operating panel, so multiple instruments may be inserted to be operated simultaneously. The formation of a single-hole multi-passage configuration reduces incisions on the abdominal wall, reduces the wounds, alleviates the stress response resulted from the trauma, and facilitates the early recovery. The middle portion of the soft connecting portion is in spherical shape, while two ends of the soft connecting portion are circular openings. The spherical middle portion of the soft connecting portion has a diameter larger than that of the circular openings at the two ends of the soft connecting portion. The middle portion of the soft connecting portion inflates to form a sphere, so that the middle portion of soft connecting portion in the natural state or pneumoperitoneum state bulges slightly. Therefore, it is possible to avoid the instruments from scratching the middle portion of the soft connecting portion. In addition, if required, the operating panel will rotate clockwise or counterclockwise around the axis of the device within a certain range, so the inflation of the middle portion of the soft connecting portion is advantageous for increasing the space for the rotation of the operating panel around axis of the device, and a certain space still can be left after rotation. The sleeve has an enough inner space, which allows the laparoscope and other two common instruments to enter the abdominal cavity through the sleeve and the laparoscope may freely move around the stomach under the cooperation of other operating holes, the laparoscope may be further moved to other operating holes and then enter a tubular anastomat with a diameter of 25 mm through the device to realize the gastrointestinal end-to-side anastomosis. The laparoscope may be removed from the pneumoperitoneum sealing device temporarily in due time. Under the illumination guide of the laparoscope through the operating holes on the abdominal wall, the cost of consumables may be saved by dividing a specimen via a straight cutting closer in laparotomy.

Preferably, a tension device, for fixing or removing the sleeve, attached to the sleeve and adjacent to the soft connecting portion, the tension device comprising a medical woven rope or an elastic silica gel belt. The tension device plays a role of tensioning and fixing, when the sleeve is inserted into an abdominal incision, to prevent the sleeve from continuing entering the abdominal cavity, and serves as a component for applying a force when the sleeve is retreated from the abdominal cavity. Particularly when the thickness of the abdominal wall is larger than the height of the sleeve, only the tension device is still exposed outside, which is convenient for the sleeve to retreat from the abdominal cavity. Other components meeting the medical transfer force may also be used as the tension device.

Preferably, the sleeve has a cylindrical shape, the blocking flange is perpendicular to an axis of the sleeve, the handles are parallel to the blocking flange, and each handle and the corresponding clamping portion are distributed along the axis of the sleeve. When the sleeve is to be inserted into an incision, two pairs of forceps are used, each pair of forceps corresponding to one clamping portion, one foot of each forcep is inserted from the hole of the corresponding handle, while the other foot thereof passes through the outside of the handle and then two feet of the forcep converge and clamp at the clamping portion.

Preferably, the sleeve has a length between 35-45 mm, the sleeve has a diameter that is 32 mm, or 25 mm or 20 mm, the blocking flange has a radial width in the range of 8-12 mm, and the cylindrical shape of the sleeve where the clamping portions are not jointed has a thickness is less than a thickness of a wall of the cylindrical shape where the clamping portions are disposed. The width of the blocking flange should be suitable for the bottom end of the sleeve to insert into the incision and should be able to prevent the sleeve from retreating from the abdominal cavity after restoring. To be convenient to insert the sleeve into an incision, there is a thin portion having a less thickness on the wall of the cylindrical shape of the sleeve. This thin portion is easy to deform and convenient for the two pairs of forceps to apply a force.

Preferably, each clamping portion is H-shaped, cross-sections of two side walls of each clamping portion are wedge-shaped, a higher side of the side walls of each clamping portion is adjacent to the external surface of the sleeve, a middle cross bar of the H-shaped clamping portion is perpendicular to a radial line of the blocking flange. As the clamping portions are wedge-shaped, the clamping portion may reinforce the blocking flange and prevent the sleeve from retreating from the abdominal cavity due to insufficient stop force. The clamping portion may be in other shapes, for example, grooved-shaped or crisscross-shaped.

Preferably, the two side walls of each clamping portion are sloped relative to a top surface of the blocking flange. The slope transition prevents the abrupt change in height from resulting in leaks on the inner wall of the abdominal cavity.

Preferably, each clamping portion is I-shaped and perpendicular to a radial line of the blocking flange, two ends of each I-shaped clamping portion and a top surface of the blocking flange are in smooth transition. The smooth transition may be slope transition or cambered transition.

Preferably, the operating panel comprises a shell, a column, and a plurality of sealing components, the shell having a through hole for receiving the column, and the sealing components are disposed inside the column, the shell has an annular edge defined inside the through hole for engaging the sealing components. The annular edge of the shell engaging the sealing components mainly refers to engaging the periphery of the sealing components, so that the air leakage may be avoided on the periphery of the sealing components.

Preferably, the column has a center, a top, and a bottom and a recess is provided at the center of the column, and the sealing components comprises a multilayer overlapped configuration disposed inside the recess; the sealing components comprises a plate, a sealing cap and an obturator, for sealing the plurality of sealed operating holes placed sequentially inside the column, the operating holes are formed on each layer of sealing components, and the corresponding operating holes on each layer of sealing components are aligned throughout the operating panel. An air inlet three-way switch is provided on the operating panel as required. The sealing components of a multilayer overlapped configuration play a role of sealing, and particularly seal well the periphery of the operating holes. The obturator and the sealing cap are made of silica gel to have elasticity, and form the seal if squeezed. The plate is made of elastics to have hardness for conveniently connection and positioning. The air inlet three-way switch is connected to a pneumoperitoneum pipe and feeds air into the abdominal cavity via a pneumoperitoneum machine.

Preferably, the obturator has a plurality of elastic sealing membranes extending downwardly from each operating hole, an aperture with a diameter less than that of a corresponding operating instrument, is provided in the center of each sealing membrane, a pair of folio valves are provided on an inner wall of each sealing membrane. When an instrument is inserted into an operating hole, the elastic sealing membranes closely cover the instrument to prevent gas from leaking from the periphery of the instrument. When the instrument is retreated from the operating hole, the valves are closed to avoid air leakage.

Preferably, the recess of the column has a supporting portion integrated with the column, the supporting portion also has a plurality of operating holes corresponding to the operating holes on the sealing components, the obturator is located on the supporting portion with each sealing membrane inserted into the corresponding operating hole of the supporting portion, a hard plastic plate with a plurality of operating holes is provided between the obturator and the sealing cap, the hard plastic plate has a plurality of annular walls extending upwardly and downwardly and respectively inserting into the corresponding operating hole of the sealing cap and of the obturator to seal the corresponding operating hole, and the hard plastic plate is provided with two annular raised edges extending upwardly and downwardly for sealing the sealing cap and of the obturator. The supporting portion is used for supporting the sealing components, and also positioning the sealing components via the annular edge of the shell. The plate, the sealing cap and the obturator are all flexible and easy to deform. The additionally arrangement of the hard plastic plate may avoid too large amount of deformation. The annular walls and annular raised edges of the hard plastic plate all are provided to squeeze and seal the periphery of the operating holes and the periphery of the sealing components.

Preferably, the plate, the sealing cap, the hard plastic plate and the obturator are all provided with a plurality of connecting holes, the supporting portion is provided with a plurality of sockets corresponding to the connecting holes, the top of the inner wall of each socket is provided with a stopping protrusion; a cover, with a bottom surface and a plurality of the operation holes, is provided on top the plate, a plurality of inserting rods corresponding the connecting holes vertically extends downwardly from the bottom surface of the cover, each inserting rod has a protruding end matching with the stopping protrusion, each inserting rod passes through corresponding connecting holes on the plate, on the sealing cap, on the hard plastic plate and on the obturator with the protruding end inserted into a corresponding socket of the supporting portion and stopped by the stopping protrusion, a gap is formed between the inner wall of each socket and each inserting rod for the protruding end to retreat from the socket. The inserting rods pass through the corresponding connecting holes, and then the ends of the insert rods are inserted into the corresponding sockets, The matching of the protruding end and the stopping protrusion forms reverse locking, thus to prevent the cover from being detached randomly. The fitting of the inserting rods and the sockets enables the cover to compress the leaks on the periphery of the operating holes, thus to avoid air leakage. The gap formed between the inner wall of each socket and each inserting rod for the protruding end to retreat from the socket enables each protruding end to rotate inside the corresponding socket and separate the end of the inserting rod from the cover. When the inserting rod rotate by 180°, the protruding end is separated from stopping protrusion, so that the inserting rod is retreated from the socket, and each layer of the sealing components may be disassembled.

Preferably, the shell has a bottom and a triangular shape with a plurality of corners, three connecting protrusions extend vertically from the bottom of the shell at each corner, three vertical grooves, each vertical groove matching with a connecting protrusion, and three transverse grooves, each traverse groove matching with a connecting protrusion, are provided at the column, each transverse groove comprises an arc portion close to the shell and communicated with the corresponding vertical groove and a parallel portion parallel to the shell, a stopping bulge, for stopping a connecting protrusion, is formed where the arc portion meets the parallel portion. The fitting between the connecting protrusions of the shell, the vertical grooves and the transverse grooves performs locking with each other. The connecting protrusions of the shell are inserted into the corresponding vertical grooves at first, and then rotated by a certain angle to the horizontal positions of the transverse grooves. During this process, the annular edge of the shell gradually squeezes the sealing components and finally connects to the column.

Preferably, a hose may be inserted into one of the operating holes on the operating panel. The hose is connected to a three-way switch. One end of the hose is connected to a clamping portion with suitable intensity. The hose may realize exhausting, blood suction and water filling through the three-way switch, so it is unnecessary to exchange instruments frequently, and the time for surgery may be thus saved. The hose is placed near an operating area during the surgery, so good smoke discharging is realized. As the clamping portion of the hose has suitable intensity, the lumen will not be closed completely when the laparoscopic instrument clamps the hose end to a target position. The lumen may be also closed completely if a slightly larger force is applied to the instrument, so that the sharp drop of the abdominal pressure caused from continuous aspiration is avoided.

Another scheme of the operating panel is as follows: the operating panel includes a panel body, each operating hole on the operating panel penetrates through the entire panel body and has a constant diameter, each operating hole has a threaded inner wall for engaging a changeover accessory with a small-diameter hole or a closure accessory; each changeover accessory comprises a hard cylinder having an inner wall and external threads for engaging the inner wall of each operating hole, and a soft inner wall extending from the inner wall of the hard cylinder to a center of the hard cylinder and defining the small-diameter hole; each closure accessory comprises a hard cylinder with external threads fitted with the inner wall of each operating hole. Each operating hole on the operating panel has a constant diameter, which simplifies the configuration of the panel body and the molds for manufacturing the panel body, and reduces the cost. Different changeover accessories of the panel body may be selected and the holes are changed to have different diameters for fitting the sealing requirements of instruments in different sizes. During the operating, an instrument directly touches with the inner wall of a changeover accessory rather than the panel body, the possibility of damage of the panel body by the instrument is reduced, and the safety of the panel body is ensured. Meanwhile, only the changeover accessories need to be replaced, so the operating cost is reduced. The operating holes may have a diameter fitting the largest instrument or larger than the required maximum diameter, and are then changed to the required maximum holes by the changeover accessories. The closure accessories are used for closing the operating holes to avoid the air leakage of abdominal cavity because the idle operating holes are not sealed. Particularly in the case when the internal leakage-proof valves are damaged after repeated use and in the open state, the passages will have air leakage, but will have no air leakage after any instrument enters the operating holes. Closing by closure accessories prolongs the service life of the plate. The hard cylinders of the changeover accessories are in threaded connection with the panel body. The hard cylinders enhance the intensity of the threaded connection. The hard cylinders of the changeover accessories are generally made of medical plastics. The inner walls of the changeover accessories are made of soft materials for improving the deformability. The small-diameter holes fit different instruments. The diameter of the small-diameter holes of the changeover accessories generally meets instruments having a diameter of 5-8 mm.

Preferably, each soft inner wall has a thickness that gradually decreases from the inner wall to the center of each hard cylinder, each small-diameter hole has a diameter adapted to an instrument to be used, and smaller than required by the instrument to be used. The soft inner wall has a thinner thickness in the center of the hard cylinder while the soft inner wall has a thicker thickness at two sides of the inner wall of the hard cylinder, it is difficult to be damaged by the instrument and meanwhile can change the direction along with the instrument, without influencing the flexibility.

Preferably, a mouth with a small pore at the center is formed at the bottom of each soft inner wall extending downwardly around each small-diameter hole, the small pore has a diameter smaller than that of the small-diameter hole. The folded mouth form a taper. The folding direction is away from the end of the corresponding operating hole. When an instrument is inserted into the small pore, the contact area with the instrument increases, and the reliability of prevention of air leakage is enhanced. Meanwhile, during the process in which the instrument is inserted or retreated, the mouth has a function of adjustment, so that the sliding friction between the soft inner wall and the instrument is reduced, and the possibility of damage is reduced.

Preferably, the panel body is shaped like a frustum cone with a smaller-diameter end and a bigger-diameter end, the smaller-diameter end of the panel body is formed with an instrument working passage communicated with the operating holes; the panel body is formed with a plurality of pairs of sealing valves extending downwardly at the bottom of the operating holes, and each pair of sealing valve has an opening. The arrangement of the working passage shortens the depth of the operating holes, and thus avoids the interference with the inner walls of the operating holes during the rotation of the instrument. The operating holes are used as a maximum instrument access passage. When no instruments enter the operating holes, the sealing valves are used as the unique sealing component, the changeover accessories are provided in the operating holes, the mouths provided on the changeover accessories serve as first seals. When an instrument enters the passage, the sealing valves play the sealing function with good effect in sealing.

Preferably, the top surface of the hard cylinder is provided with a plurality of rotary contact portions, which are a plurality of cylinders protruding upwardly or a plurality of circular recesses. The rotary contact portions bring convenience for the changeover accessories to rotate inside the operating holes and are mainly used for assembling or dissembling of the changeover accessories or the closure accessories. The rotary contact portions may be in other configuration, for example, butterfly buttons, prolonged extension ends or components with handles.

Preferably, the soft connecting portion has a top end and a bottom end, both the top end and the bottom end are formed with clamping rings, each clamping ring with an arc surface protruding toward the axis of the soft connecting portion; the operating panel and the sleeve are both provided with a receiving recess for receiving the clamping rings. The clamping rings are protruded, while the receiving grooves are recessed, so they match with each other properly, and the soft connecting portion has elasticity, thus Sealing is realized after matching; The arc surfaces bring convenience to insert the clamping rings into the receiving grooves, and the straight surfaces properly stops the soft connecting portion retreating from the receiving grooves, so that the accident of slipping is avoided.

Compared with the prior art, in the present invention, the sleeve is inserted into the wound of the abdominal wall, the blocking flange is positioned inside the abdominal cavity and the soft connecting portion is positioned outside the abdominal cavity. The blocking flange stops and prevents the sleeve from retreated from the wound. The sleeve is fixed by the tension device, and the elastic force generated by the sleeve squeezes the wound wall for sealing. The operating panel may rotate around the axis of the soft connecting portion within a small range, so it is convenient for the operations of instruments, and the operating holes with seals may avoid air leakage of the abdominal cavity. The multilayer overlapped configuration inside the operating panel has good air-tightness. A plurality of operating holes is provided on the operating panel and an instrument may be inserted into the abdominal cavity through the operating holes, so the wounds of the abdominal cavity are reduced. The one-hole multi-passage configuration is convenient for surgery and also saves the surgical cost. A working passage is provided for allowing instruments with a diameter of 25 mm to enter the pneumoperitoneum, so that it is convenient for a tubular anastomat to enter the pneumoperitoneum to implement the gastrointestinal end-to-side anastomosis.

The components list with the corresponding reference number: the shell-1, the operating hole-2, the sealing components-3, the soft connecting portion-4, the blocking the flange-5, the sleeve-6, the elastic silica gel belt-7, the clamping portion-8, the cross bar-9, the handle-10, the hole-11, the cover-12, the step-13, the inserting rod-14, the annular guiding edge-15, the plate-16, the sealing cap 17, the annular wall-18, the annular raised edge-19, the hard plastic plate-20, the obturator-21, the recess-22, the deformation portion-23, the air inlet-24, the connecting hole-25, the annular edge-26, the connecting protrusion-27, the column-28, the supporting portion-29, the clamping ring-30, the receiving recess-31, the socket-32, the stopping protrusion-33, the protruding end-34, the vertical groove-35, the transverse groove-36, the sealing membrane-37, the guiding slope-38, the slope-39, the stopping bulge-40, the panel body-41, the cylinder-42, the changeover accessory-43, the small-diameter hole-44, the air inlet-45, the instrument working passage-46, the soft inner wall-47, the small pore-48, the mouth-49, the hard cylinder-50, the closure accessory-51, the valve-52.

DETAILED DESCRIPTION OF THE PREFERRED EMBODIMENT

To enable a further understanding of the innovative and technological content of the invention herein, refer to the detailed description of the invention and the accompanying drawings below:

Embodiment 1: a device, for sealing a single incision in a laparoscopic surgery, comprises: a top portion; a bottom portion; an operating panel located on the top portion of the device and with a plurality of sealed operating holes 2, a sleeve with suitable elasticity located on the bottom portion of the device, having an external surface and a top end and a bottom end, for fitting into the single incision, a soft connecting portion 4 for connecting the operating panel to the sleeve 6.

Figure 1:
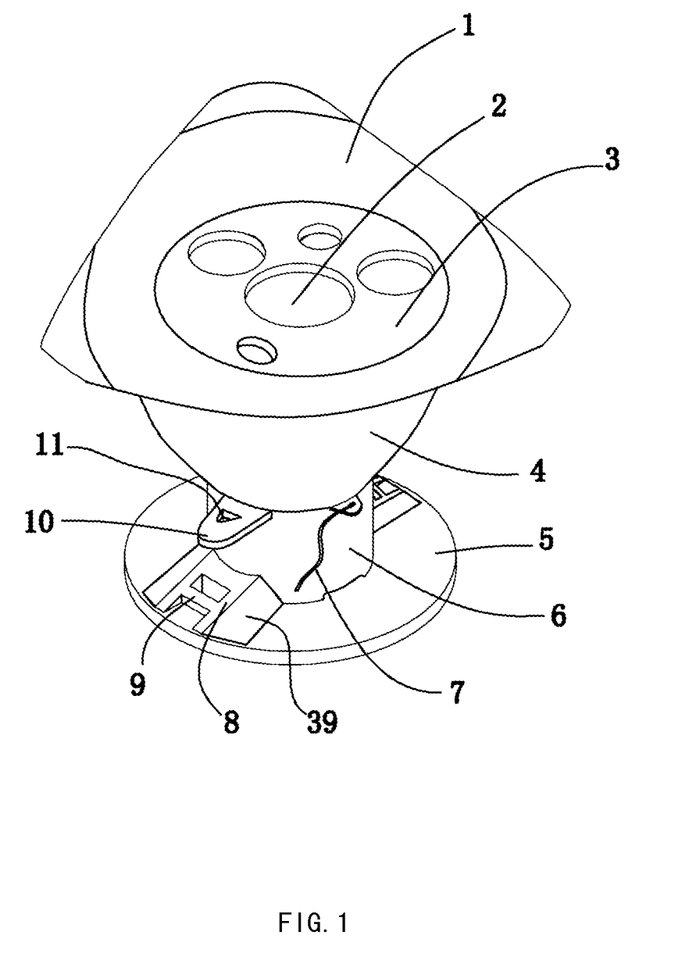
FIG. 1 is a perspective view of a device in accordance with a first embodiment of the present invention.
Figure 2:
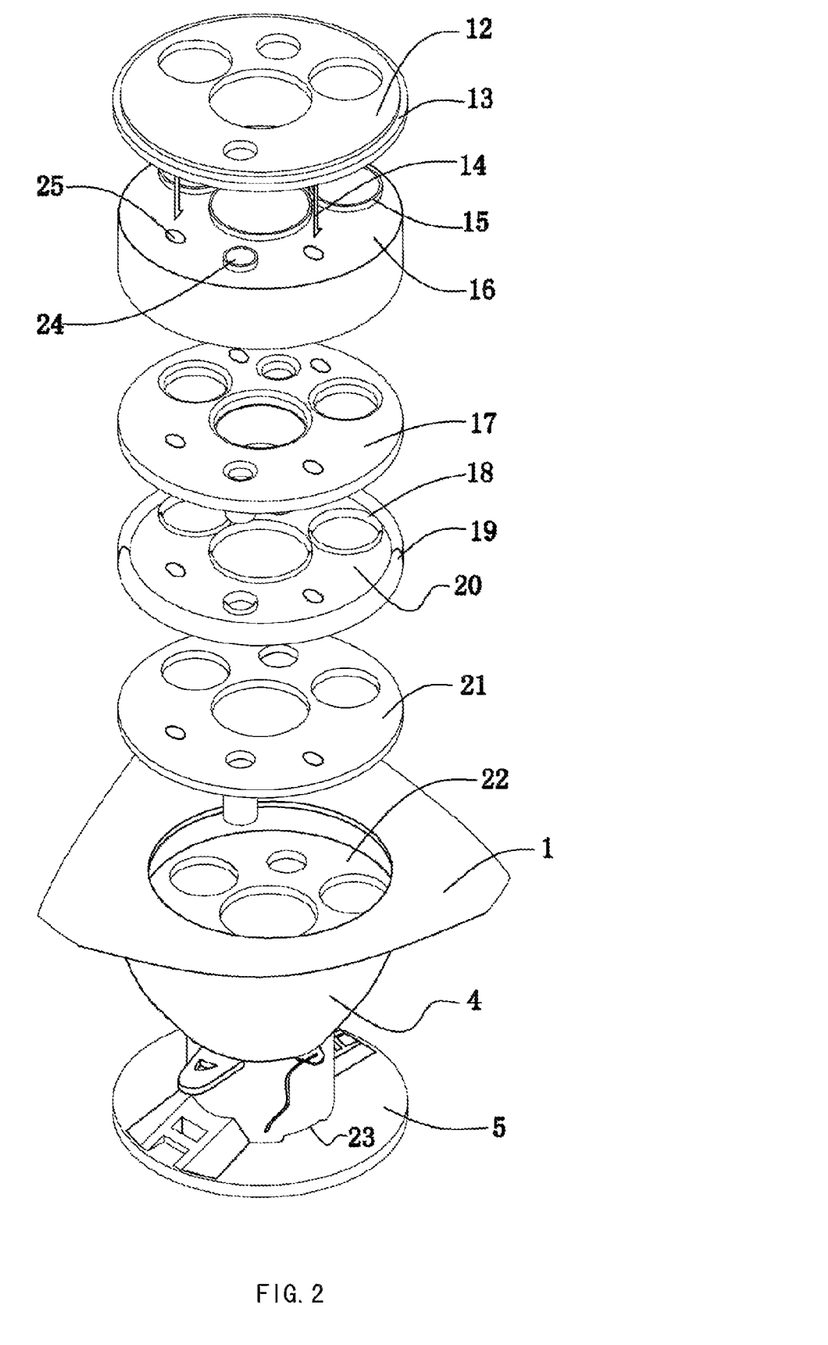
FIG. 2 is an exploded perspective view of the device in accordance with the first embodiment of the present invention.
Figure 3:
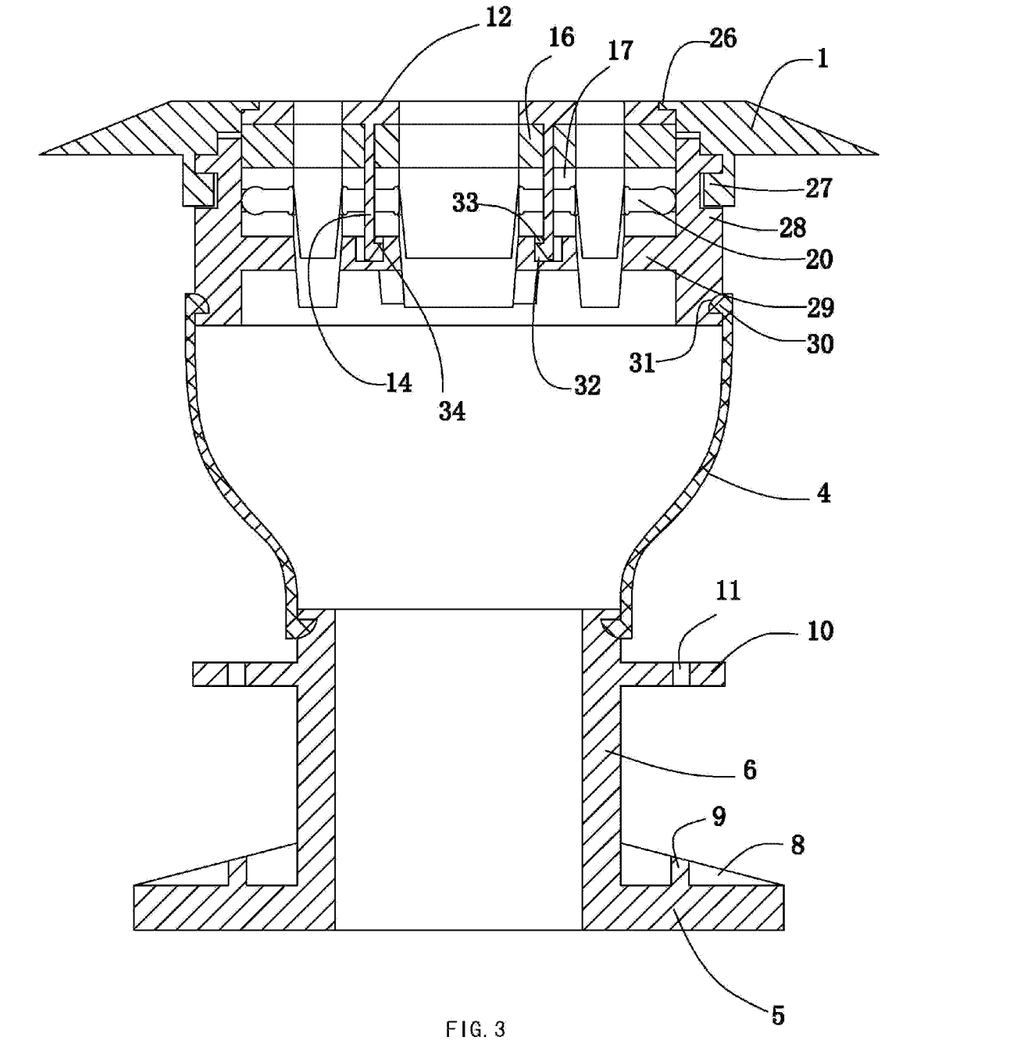
FIG. 3 is a sectional view of FIG. 1.
Figure 4:
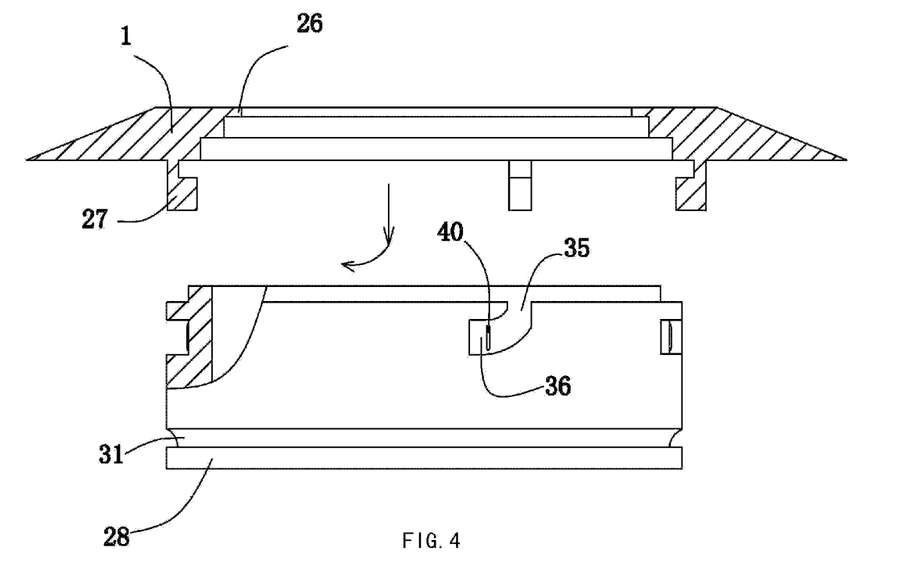
FIG. 4 is a exploded sectional view of the shell and the column in accordance with the first embodiment of the present invention.
Figure 5:
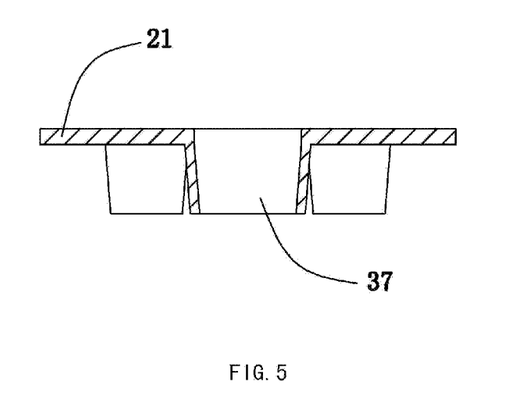
FIG. 5 is a sectional view of the obturator in accordance with the first embodiment of the present invention.
Figure 6:
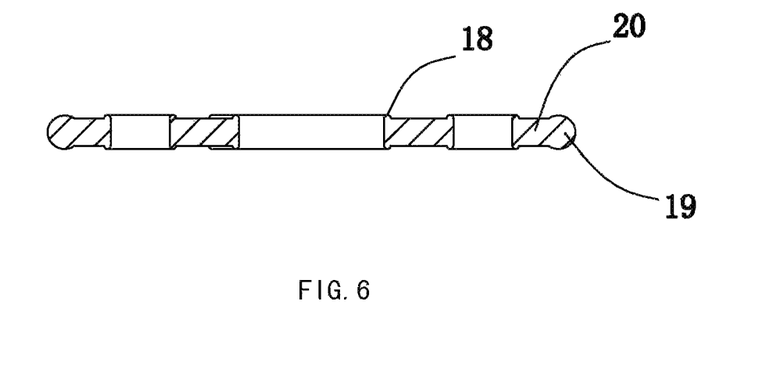
FIG. 6 is a sectional view of the hard plastic plate in accordance with the first embodiment of the present invention.
Figure 7:
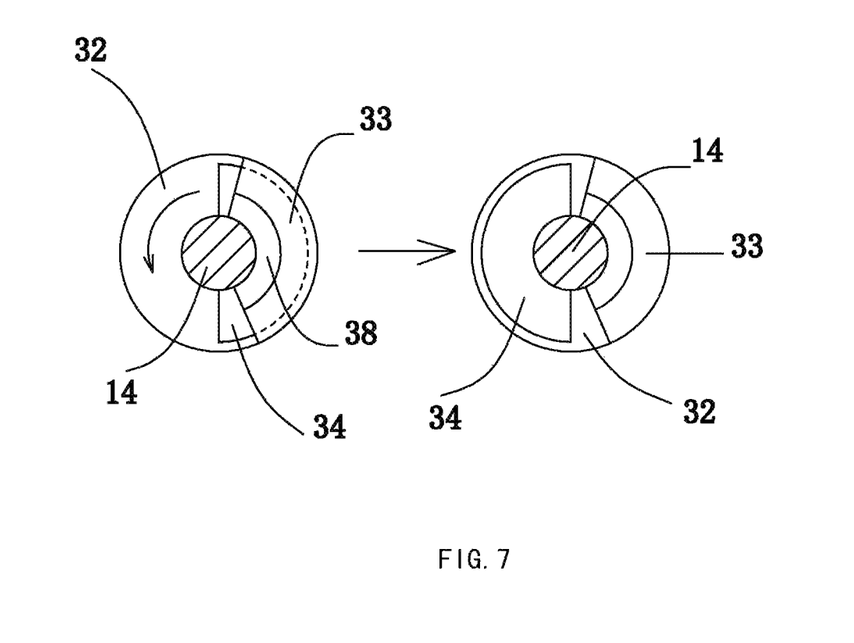
FIG. 7 is an illustrating view of the inserting rod, the socket, the protruding end and the stopping protrusion, showing the rotation situation of the inserting rod relative to the socket.

The operating panel comprises a shell 1, a column 28, and a plurality of sealing components 3, the shell has a through hole for receiving the column 28, and the sealing components 3 are disposed inside the column 28. The shell has a bottom and a triangular shape with three corners, three connecting protrusions extend vertically from the bottom of the shell at each corner via three connecting arms (referring to FIG. 4). The three connection protrusions are arranged symmetrically in the shell, and are protruded towards the axis of the shell relative to the connecting arms. The shell has an annular edge defined inside the through hole. Three vertical grooves, each vertical groove matching with a connecting protrusion, and three transverse grooves, each traverse groove matching with a connecting protrusion, are provided at the column, each transverse groove comprises an arc portion close to the shell and communicated with the corresponding vertical groove and a parallel portion parallel to the shell, a stopping bulge 40, for stopping a connecting protrusion, is formed where the arc portion meets the parallel portion. A recess 22 is provided at the center of the column 28, and the sealing components comprise a multilayer overlapped configuration disposed inside the recess. The recess of the column has a supporting portion 29 integrated with the column, the supporting portion also has a plurality of operating holes corresponding to the operating holes on the sealing components. The supporting portion is provided with four sockets 32 having sealed bottoms (referring to FIG. 3), and are distributed around the operating holes. The sealing components comprises a cover 12, a plate 16, a sealing cap 17, a hard plastic plate 20 and an obturator 21, for sealing the plurality of sealed operating holes 2 placed sequentially inside the column, the operating holes re formed on each layer of sealing components, and the corresponding operating holes on each layer of sealing components are aligned throughout the operating panel (referring to FIG. 2). The obturator has a plurality of elastic sealing membranes 37 extending downwardly from each operating hole (referring to FIG. 5), an aperture with a diameter less than that of a corresponding operating instrument, is provided in the center of each sealing membrane, a pair of folio valves are provided on an inner wall of each sealing membrane. The obturator is located on the supporting portion with each sealing membrane inserted into the corresponding operating hole of the supporting portion. The sealing cap has a plurality of elastic sealing membranes 37 extending downwardly from each operating hole, each sealing membrane is inserted into the corresponding operating hole of hard plastic plate and extends into the corresponding operating hole of the obturator (referring to FIG. 3). The hard plastic plate has a plurality of annular walls 18 extending upwardly and downwardly and the hard plastic plate is provided with two annular raised edges 19 extending upwardly and downwardly (referring to FIG. 6). The two annular walls 18 respectively inserts into the corresponding operating hole of the sealing cap and of the obturator to seal the corresponding operating hole, and the two annular raised edges extends upwardly and downwardly for sealing the sealing cap and of the obturator. Each operating hole of the plate has an annular guiding edge 15, the guiding edges are respectively inserted into the corresponding operating hole of the cover when the cover covers the plate. The plate is provided with a step 13, the sealing components are placed into the recess of the column, the shell covers the top of the column, the connecting protrusions are respectively inserted into the corresponding vertical groove, and then the shell is rotated to make the connecting protrusions move along the transverse grooves, moreover, the shell has an annular edge for engaging the step of the cover, so that the sealing components is tightly pressed into the recess. A plurality of inserting rods 14 corresponding to the sockets vertically extend downwardly from the bottom surface of the cover, the plate, the sealing cap, the hard plastic plate and the obturator are all provided with a plurality of connecting holes relative to the corresponding socket, the end of each inserting rod passes through the corresponding connecting hole and is inserted into a corresponding socket to be positioned tightly, so that the gaps between the operating holes may be compressed by the cover. The top of the inner wall of each socket is provided with a stopping protrusion 33, the central angle of each stopping protrusion occupying the sockets is 145°. Each stopping protrusion has a guiding slope 38 on the top surface, each inserting rod has a protruding end 34 matching with the stopping protrusion, the central angle of each protruding end occupying the corresponding inserting rod is 180°, a gap is formed between the inner wall of each socket and each inserting rod for the protruding end to retreat from the socket. The gap is convenient for the inserting rods to generate elastic deformation, so that the protruding end are inserted into the sockets and match with the stopping protrusion for being positioned. When the ends of inserting rods have to retreat from the cover and the inserting rods are rotated by 180°, the protruding ends are separated from the stopping protrusion, so that the inserting rods may retreat from the sockets. In this way, the disassembly of the operating panel is accomplished (referring to FIG. 7). An inlet 24 for air to pass through is provided on the operating panel according to the requirements of surgery, the inlet communicates with a three-way switch to conveniently inflate the pneumoperitoneum and establish a pneumoperitoneum pressure.

The bottom portion of external surface of the column is provided with a receiving recess 31 (referring to FIG. 3 and FIG. 4), the receiving recess has an arc top surface and a horizontal bottom surface that vertical to the axis of the column. The top end of the soft connecting portion is formed with a clamping ring 30 protruding towards the axis of the soft connecting portion. The shape of the clamping ring is fitted with that of the receiving groove. The clamping ring is blocked into the receiving groove for realizing sealing connection. The top end of the sleeve is provided with a receiving recess 31, the receiving recess has an arc bottom surface and a horizontal top surface that vertical to the axis of the sleeve. The bottom end of the soft connecting portion is formed with a clamping ring 30 protruding towards the axis of soft connecting portion. The clamping ring is blocked into the receiving groove for realizing sealing connection.

Two symmetrical handles 10 and two symmetrical hangers are attached to the external surface of the sleeve where the sleeve connects to the soft connecting portion. Each handle is vertical to the corresponding hanger. Each handle and each hanger have a hole in the center. Each hole of the hangers is fixedly connected with an elastic silica gel belt 7. The sleeve 6 has a cylindrical shape for fitting into the single incision. A blocking flange 5 is attached to the bottom end of the sleeve and perpendicular to an axis of the sleeve. Two clamping portions 8 disposed on the blocking flange under the two handles. The handles are parallel to the blocking flange, and each handle and the corresponding clamping portion are distributed along the axis of the sleeve. Each clamping portion 8 is H-shaped, cross-sections of two side walls of each clamping portion are wedge-shaped, a higher side of the side walls of each clamping portion is adjacent to the external surface of the sleeve, a middle cross bar 9 of the H-shaped clamping portion is perpendicular to a radial line of the blocking flange. The cross bars correspond to the holes of the handles. Two side walls of each clamping portion are in slope 39 relative to a top surface of the blocking flange, so that it is ensured that no abrupt change of height will exist on the a top surface of the blocking flange. The sleeve has a length of 40 mm, the sleeve has a diameter that is 32 mm, or 25 mm or 20 mm according to the surgical specification, and the blocking flange has a radial width in the range of 10 mm. the cylindrical shape of the sleeve where the clamping portions are not jointed are deformation portions 23, which have a thickness is less than a thickness of a wall of the cylindrical shape where the clamping portions are disposed.

The sleeve, the soft connecting portion, the obturator and the sealing cap are made of medical silica gel, while the shell, the column, the hard plastic plate, the plate and the cover are made of plastics. If the sleeve is made of medical polyurethane, the top end of the sleeve is made of medical plastics used for secondary forming, to enhance its hardness.

During the operation, two pairs of forceps are used and aligned to the two handles of the sleeve, respectively. One foot of each pair of forceps is inserted from a hole of a handle, while the end of this foot converges with the end of the other foot of this pair of forceps and clamps the corresponding cross bar of the clamping portion. The other pair of forceps is operated in a similar way to clamp the cross bar of the other clamping portion. The two pairs of forceps are inserted into an abdominal incision. The blocking flange is warped under the block of the abdominal wall. When the deformation portions generate deformation, and the blocking flange enters the abdominal cavity, the sleeve and the blocking flange restore to the original shapes, and the blocking flange adheres to the inner skin wall of the abdominal cavity to form a stop configuration. The elastic silica belts are fixed outside the abdominal wall for fixing the sleeve. After the sleeve is fixed, the surgery may be performed according to its progress.

Figure 8:
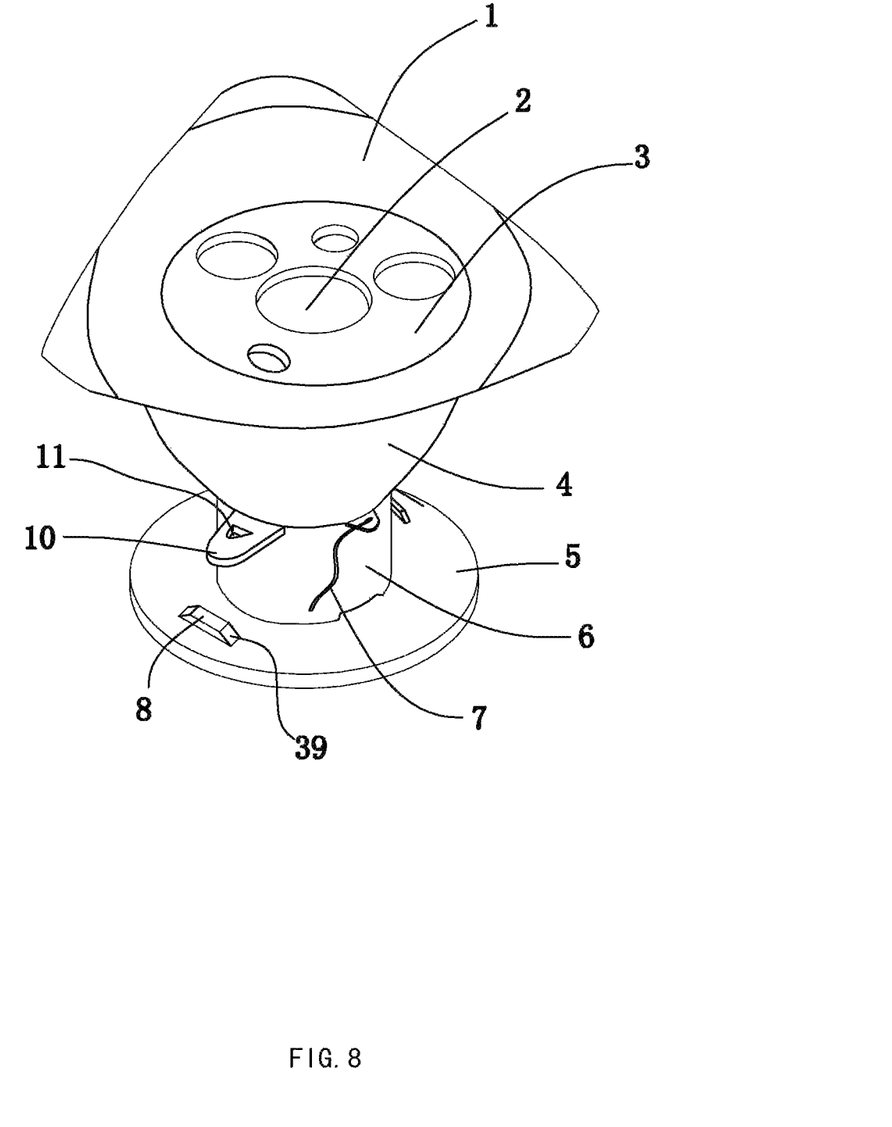
FIG. 8 is a perspective view of a device in accordance with a second embodiment of the present invention.

Embodiment 2: a device for sealing a single incision in a laparoscopic surgery (referring to FIG. 8), comprises two I-shaped clamping portions 8 disposed on the blocking flange 5 under the two handles. Each clamping portion is perpendicular to a radial line of the blocking flange, two ends of each I-shaped clamping portion and a top surface of the blocking flange are in sloped transition 39. Other configurations of the device refer to the embodiment 1.

Embodiment 3: a single-hole multi-passage operating panel for a laparoscopic surgery (referring to FIG. 9 and FIG. 10) includes a panel body 41 shaped like a frustum cone, four operating holes on the operating panel penetrates through the entire panel body and an air inlet 45 is provided on the panel body. The panel body has a smaller-diameter end and a bigger-diameter end, the smaller-diameter end of the panel body is formed with an instrument working passage 46, the bigger-diameter end of the panel body is formed with the operating panel. The operating holes are disposed on the operating panel and communicated with the working passage.

Figure 9:
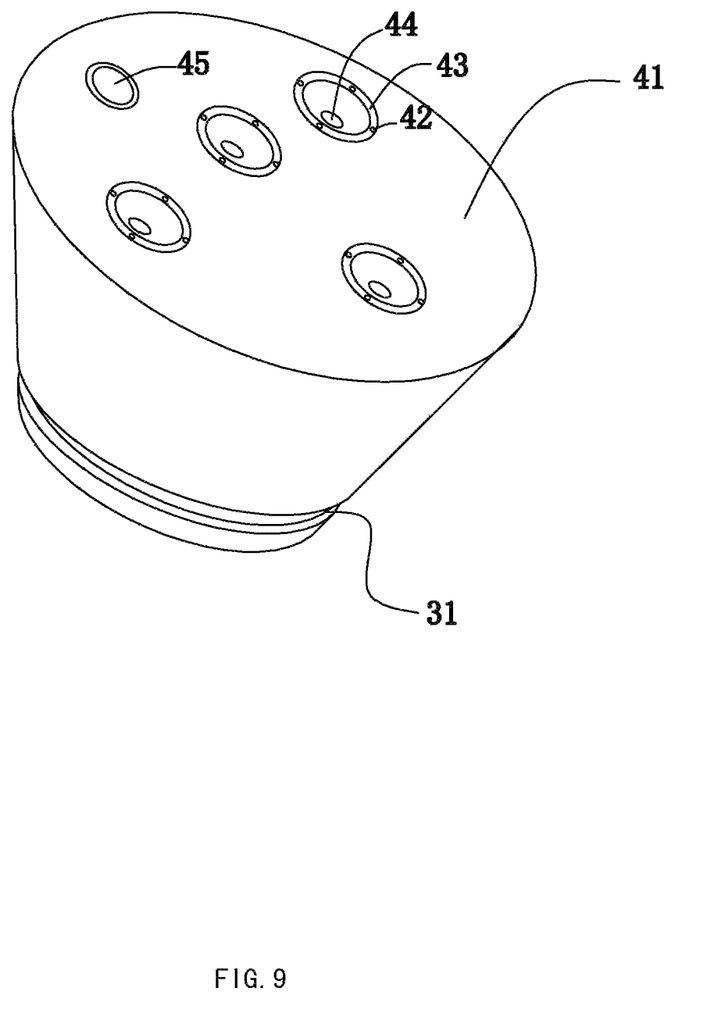
FIG. 9 is a perspective view of an operating panel of a device in accordance with a third embodiment of the present invention.
Figure 10:
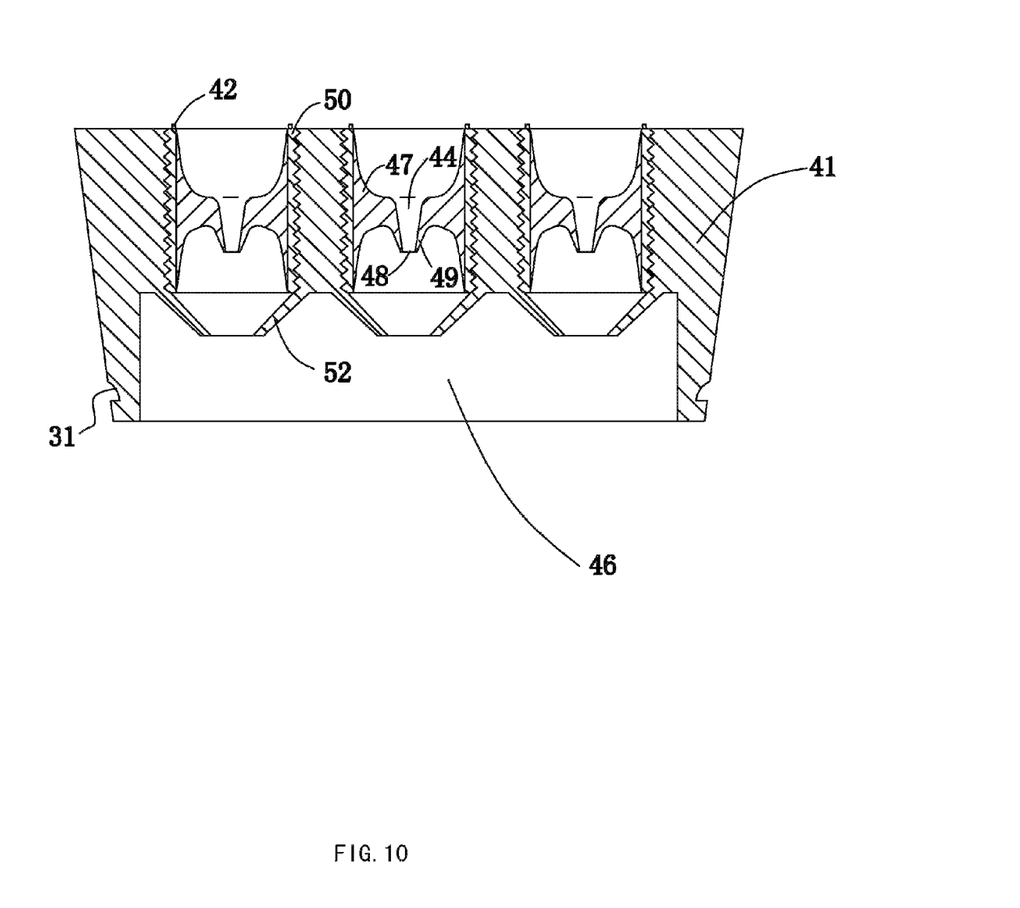
FIG. 10 is a sectional view of FIG. 9.

Each operating hole has a constant diameter of 15 mm. The panel body is formed with a plurality of pairs of sealing valves 52 in conical shape that extends downwardly at the bottom of the operating holes, and each pair of sealing valve has an opening. Each operating hole has a threaded inner wall for engaging a changeover accessory 43 with a small-diameter hole. Each changeover accessory comprises a hard cylinder 50 having an inner wall and external threads for engaging the inner wall of each operating hole, and a soft inner wall 47 extending from the inner wall of the hard cylinder to a center of the hard cylinder and defining the small-diameter hole 44. Each soft inner wall has a thickness that gradually decreases from the inner wall to the center of each hard cylinder, each small-diameter hole has a diameter adapted to an instrument to be used, and smaller than required by the instrument to be used. A mouth 49 with a small pore 48 at the center is formed at the bottom of each soft inner wall extending downwardly around each small-diameter hole, the small pore has a diameter smaller than that of the small-diameter hole. The top surface of the shell is provided with four cylinders 42 protruding upwardly and at an interval of 90°.

Figure 11:
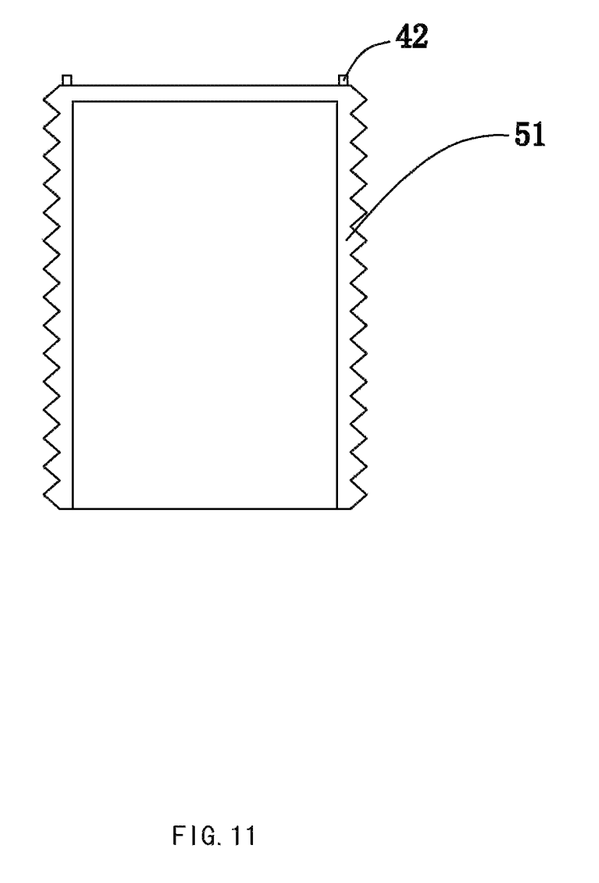
FIG. 11 is a sectional view of the closure accessory of the device in accordance with the third embodiment of the present invention.

The panel body is also provided with closure accessories 51 (referring to FIG. 11). Each closure accessories comprises a hard cylinder with external threads, and the top surface of the hard cylinder is a closed configuration. The top surface of the hard cylinder is provided with a plurality of cylinders 42 protruding upwardly and at an interval of 90°. The closure accessories are threaded in the operating holes.

The small-diameter hole has a diameter that is 3 mm, or 4 mm or 5 mm according to the operation specification. The specific size adapted to an instrument to be used in a surgery.

Five operating holes may be also provided on the operating panel. Other than the operating holes required in practical operation, the rest operating holes are sealed by the closure accessories. The required operating holes are in threaded engagement with corresponding changeover accessories, and small-diameter holes of a suitable diameter are used.

The above embodiments are merely preferred solutions of the present invention and are not intended to limit the present invention in any form. Other variations and modifications may be made without departing from the technical solutions defined by the claims.

The invention claimed is:

1. A device, for sealing a single incision in a laparoscopic surgery, comprising:
   a top portion;
   a bottom portion;
   an operating panel located on the top portion of the device and with a plurality of sealed operating holes,
   a sleeve with suitable elasticity located on the bottom portion of the device, having an external surface and a top end and a bottom end, for fitting into the single incision,
   a soft connecting portion for connecting the operating panel to the sleeve; and
   a blocking flange attached to the bottom end of the sleeve,
   wherein the operating panel comprises a shell, a column, and a plurality of sealing components, the shell having a through hole for receiving the column, and the sealing components are disposed inside the column, the shell has an annular edge defined inside the through hole for engaging the sealing components, the column has a center, a top, and a bottom, and a recess is provided at the center of the column, and the sealing components comprise a multilayer overlapped configuration disposed inside the recess;

the sealing components comprise a plate, a sealing cap and an obturator, for sealing the plurality of sealed operating holes placed sequentially inside the column, the operating holes are formed on each layer of sealing components, and the corresponding operating holes on each layer of sealing components are aligned throughout the operating panel, the obturator has a plurality of elastic sealing membranes extending downwardly from each operating hole, an aperture with a diameter less than that of a corresponding operating instrument, is provided in the center of each sealing membrane, a pair of folio valves are provided on an inner wall of each sealing membrane, and the recess of the column has a supporting portion integrated with the column, the supporting portion also has a plurality of operating holes corresponding to the operating holes on the sealing components, the obturator is located on the supporting portion with each sealing membrane inserted into the corresponding operating hole of the supporting portion, a hard plastic plate with a plurality of operating holes is provided between the obturator and the sealing cap, the hard plastic plate has a plurality of annular walls extending upwardly and downwardly and respectively inserting into the corresponding operating hole of the sealing cap and of the obturator to seal the corresponding operating hole, and the hard plastic plate is provided with two annular raised edges extending upwardly and downwardly for sealing the sealing cap and of the obturator.

2. The device of claim 1, wherein the plate, the sealing cap, the hard plastic plate and the obturator are all provided with a plurality of connecting holes, the supporting portion is provided with a plurality of sockets corresponding to the connecting holes, the top of the inner wall of each socket is provided with a stopping protrusion;

a cover, with a bottom surface and a plurality of the operation holes, is provided on top the plate, a plurality of inserting rods corresponding to the connecting holes vertically extend downwardly from the bottom surface of the cover, each inserting rod has a protruding end matching with the stopping protrusion, each inserting rod passes through corresponding connecting holes on the plate, on the sealing cap, on the hard plastic plate and on the obturator with the protruding end inserted into a corresponding socket of the supporting portion and stopped by the stopping protrusion, a gap is formed between the inner wall of each socket and each inserting rod for the protruding end to retreat from the socket.

3. The device of claim 1, wherein the shell has a bottom and a triangular shape with a plurality of corners, three connecting protrusions extend vertically from the bottom of the shell at each corner, three vertical grooves, each vertical groove matching with a connecting protrusion, and three transverse grooves, each traverse groove matching with a connecting protrusion, are provided at the column, each transverse groove comprises an arc portion close to the shell and communicated with the corresponding vertical groove and a parallel portion parallel to the shell, a stopping bulge, for stopping a connecting protrusion, is formed where the arc portion meets the parallel portion.

4. The device of claim 1, wherein the soft connecting portion has a top end, the top end is formed with clamping rings, each clamping ring with an arc surface protruding toward the axis of the soft connecting portion; the operating panel is provided with a receiving recess for receiving the clamping rings.

5. The device of claim 1, further comprising two symmetrical handles attached to the external surface of the sleeve, where the sleeve connects to the soft connecting portion, each handle having a hole, each handle having a corresponding clamping portion disposed underneath said aforementioned handle on the blocking flange.

6. The device of claim 5, wherein the sleeve has a cylindrical shape, the blocking flange is perpendicular to an axis of the sleeve, the handles are parallel to the blocking flange, and each handle and the corresponding clamping portion are distributed along the axis of the sleeve.

7. The device of claim 1, wherein the soft connecting portion, the sleeve and the blocking flange are formed integrally.

* * * * *